United States Patent
Bates et al.

(10) Patent No.: US 6,183,482 B1
(45) Date of Patent: *Feb. 6, 2001

(54) MEDICAL RETRIEVAL BASKET WITH LEGS SHAPED TO ENHANCE CAPTURE AND REDUCE TRAUMA

(75) Inventors: James S. Bates; James W. Riley, both of Bloomington, IN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/027,534

(22) Filed: Feb. 23, 1998

Related U.S. Application Data

(60) Provisional application No. 60/060,830, filed on Oct. 1, 1997, provisional application No. 60/060,819, filed on Oct. 1, 1997, and provisional application No. 60/060,821, filed on Oct. 1, 1997.

(51) Int. Cl.[7] .................................................... A61B 17/00
(52) U.S. Cl. ............................................. 606/127; 606/113
(58) Field of Search ...................................... 606/127, 128, 606/113, 170; 600/206

(56) References Cited

U.S. PATENT DOCUMENTS

| | | | |
|---|---|---|---|
| 2,556,783 | * 6/1951 | Wallace | 606/127 |
| 3,137,298 | 6/1964 | Glassman | 128/328 |
| 3,472,230 | 10/1969 | Fogarty . | |
| 3,828,790 | 8/1974 | Curtiss et al. | 128/320 |
| 3,882,872 | * 5/1975 | Douvas et al. | 606/170 |
| 3,902,498 | * 9/1975 | Niederer | 606/170 |
| 3,955,578 | 5/1976 | Chamness et al. | 128/303.15 |
| 3,996,938 | 12/1976 | Clark, III | 128/348 |
| 4,046,150 | 9/1977 | Schwartz et al. | 128/328 |
| 4,190,042 | * 2/1980 | Sinnreich | 606/206 |

(List continued on next page.)

FOREIGN PATENT DOCUMENTS

| | | |
|---|---|---|
| 56865/86 | 4/1986 | (AU) . |
| 2821048 | 11/1979 | (DE) . |
| 3213223 A1 | 10/1983 | (DE) . |
| 3407708 A1 | 9/1985 | (DE) . |
| 8707515 U1 | 9/1987 | (DE) . |
| 8707516 U1 | 10/1987 | (DE) . |
| 3620385 C1 | 1/1988 | (DE) . |
| 4025799 A1 | 2/1992 | (DE) . |

(List continued on next page.)

OTHER PUBLICATIONS

Copy of International Search Report for PCT/US98/20560 (5 pgs).

Vorwerk, Dierk et al., "Percutaneous Embolectomy: In Vitro Investigatins of the Self–expanding Tulip Sheath", Radiology (1992) 182: 415–418.

Vorwerk, Dierk et al., "Percutaneous Ballon Embolectomy with a Self–expanding Tulip Sheath: In Vitro Experiments", Radiology (1995) 197: 153–156.

*Primary Examiner*—Paul J. Hirsch
(74) *Attorney, Agent, or Firm*—Testa, Hurwitz & Thibeault, LLP

(57) ABSTRACT

A medical retrieval device, and related method, uses a basket formed by one or more legs to retrieve material such as calculi. At least one of the legs has at least an inner and a outer surface. The outer surface is an atraumatic surface such as a curved surface. The atraumatic surface can include one or more radii. The inner surface can be flat such that the leg has a D-shaped cross section. Other shapes are possible for the inner surface including a pointed shape that enhances the basket's stone crushing or breaking ability. The inner surfaces, whatever its shape, can have a rough surface (e.g., serrated, etched, toothed, etc.) for further enhancing the basket's ability to capture stones and other calculi.

27 Claims, 4 Drawing Sheets

U.S. PATENT DOCUMENTS

| | | | |
|---|---|---|---|
| 4,198,960 | 4/1980 | Utsugi | 128/6 |
| 4,203,429 | 5/1980 | Vasilevsky et al. | 128/1 R |
| 4,243,040 | 1/1981 | Beecher | 128/328 |
| 4,299,225 | 11/1981 | Glassman | 128/328 |
| 4,326,530 | 4/1982 | Fleury, Jr. | 128/303.14 |
| 4,347,846 | 9/1982 | Dormia | 128/328 |
| 4,425,908 | 1/1984 | Simon | 128/1 R |
| 4,447,227 | 5/1984 | Kotsanis | 604/95 |
| 4,486,680 | 12/1984 | Bonnet et al. | 310/323 |
| 4,557,255 | 12/1985 | Goodman | 128/7 |
| 4,590,938 | 5/1986 | Segura et al. | 128/328 |
| 4,592,341 | 6/1986 | Omagari et al. | 128/4 |
| 4,611,594 * | 9/1986 | Grayhack et al. | 606/127 |
| 4,612,931 | 9/1986 | Dormia | 128/328 |
| 4,625,726 | 12/1986 | Duthoy | 128/328 |
| 4,633,871 | 1/1987 | Shinozuka | 128/32 |
| 4,650,466 | 3/1987 | Luther | 604/95 |
| 4,682,599 | 7/1987 | Konomura | 128/328 |
| 4,691,705 | 9/1987 | Okada | 128/328 |
| 4,699,147 | 10/1987 | Chilson et al. | 128/642 |
| 4,706,671 | 11/1987 | Weinrib | 128/348.1 |
| 4,718,419 | 1/1988 | Okada | 128/303.15 |
| 4,723,549 | 2/1988 | Wholey et al. | 128/344 |
| 4,728,319 | 3/1988 | Masch | 604/22 |
| 4,768,505 | 9/1988 | Okada et al. | 128/328 |
| 4,790,812 | 12/1988 | Hawkins, Jr. et al. | 604/22 |
| 4,790,813 | 12/1988 | Kensey | 604/22 |
| 4,794,928 | 1/1989 | Kletschka | 128/344 |
| 4,807,626 | 2/1989 | McGirr | 128/328 |
| 4,873,978 | 10/1989 | Ginsburg | 128/345 |
| 4,885,003 | 12/1989 | Hillstead | 604/22 |
| 4,893,621 | 1/1990 | Heyman | 606/127 |
| 4,907,572 | 3/1990 | Borodulin et al. | 606/128 |
| 4,926,858 | 5/1990 | Gifford, III et al. | 606/159 |
| 4,927,426 | 5/1990 | Dretler | 606/128 |
| 4,927,427 | 5/1990 | Kriauciunas et al. | 606/128 |
| 4,994,079 | 2/1991 | Genese et al. | 606/206 |
| 4,998,539 | 3/1991 | Delsanti | 128/898 |
| 5,011,488 | 4/1991 | Ginsburg | 606/159 |
| 5,030,201 | 7/1991 | Palestrant | 604/22 |
| 5,041,093 | 8/1991 | Chu | 604/104 |
| 5,053,008 | 10/1991 | Bajaj | 604/104 |
| 5,057,114 | 10/1991 | Wittich et al. | 606/127 |
| 5,059,199 | 10/1991 | Okada et al. | 606/127 |
| 5,064,428 | 11/1991 | Cope et al. | 606/127 |
| 5,071,407 | 12/1991 | Termin et al. | 604/104 |
| 5,084,054 | 1/1992 | Bencini et al. | 606/113 |
| 5,098,440 | 3/1992 | Hillstead | 606/108 |
| 5,098,441 | 3/1992 | Wechler | 606/113 |
| 5,100,423 | 3/1992 | Fearnot | 606/159 |
| 5,102,415 | 4/1992 | Guenther et al. | 604/159 |
| 5,122,147 * | 6/1992 | Sewell, Jr. | 606/113 |
| 5,171,233 | 12/1992 | Amplatz et al. | 604/281 |
| 5,176,688 * | 1/1993 | Narayan et al. | 606/127 |
| 5,190,557 | 3/1993 | Borodulin et al. | 606/127 |
| 5,192,286 | 3/1993 | Phan et al. | 606/127 |
| 5,290,294 | 3/1994 | Cox et al. | 606/108 |
| 5,311,858 | 5/1994 | Adair | 128/4 |
| 5,325,848 | 7/1994 | Adams et al. | 128/20 |
| 5,329,942 | 7/1994 | Gunther et al. | 128/898 |
| 5,330,482 | 7/1994 | Gibbs et al. | 606/113 |
| 5,345,936 | 9/1994 | Pomeranz et al. | 128/642 |
| 5,354,310 | 10/1994 | Garnic et al. | 606/198 |
| 5,370,647 * | 12/1994 | Graber et al. | 606/127 |
| 5,376,100 | 12/1994 | Lefebvre | 606/180 |
| 5,421,832 | 6/1995 | Lefebvre | 604/53 |
| 5,496,330 | 3/1996 | Bates et al. | 606/127 |
| 5,499,981 | 3/1996 | Kordis | 606/41 |
| 5,522,790 * | 6/1996 | Moll et al. | 600/206 |
| 5,527,354 | 6/1996 | Fontaine et al. | 623/1 |
| 5,549,626 | 8/1996 | Miller et al. | 606/200 |
| 5,658,296 | 8/1997 | Bates et al. | 606/127 |
| 5,693,069 | 12/1997 | Shallman | 606/205 |
| 5,792,145 * | 8/1998 | Bates et al. | 606/127 |

FOREIGN PATENT DOCUMENTS

| | | |
|---|---|---|
| 32 13 223 A1 | 10/1993 | (DE) |
| 0160870 A2 | 11/1985 | (EP) |
| 0 195 444 | 9/1986 | (EP) |
| 0 428 998 A1 | 5/1991 | (EP) |
| 0 737 450 A1 | 10/1996 | (EP) |
| 2694687 | 2/1994 | (FR) |
| 2 020 557A | 11/1979 | (GB) |
| WO 91/11209 | 8/1991 | (WO) |
| 92/05828 | 4/1992 | (WO) |
| WO 94/24946 | 11/1994 | (WO) |
| 95/05129 | 2/1995 | (WO) |
| WO 96/01591 | 1/1996 | (WO) |

* cited by examiner

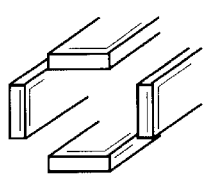
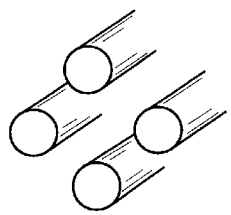
FIG. 5A　　　FIG. 5B
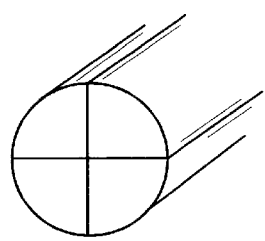
FIG. 7A
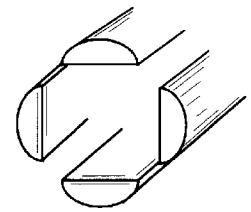
FIG. 6A
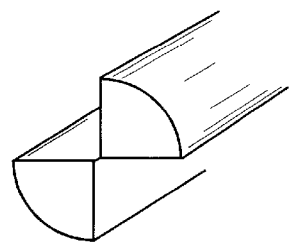
FIG. 7B
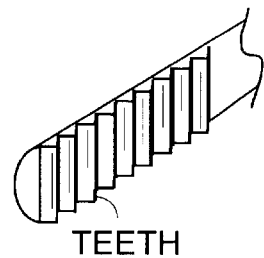
TEETH
FIG. 6B
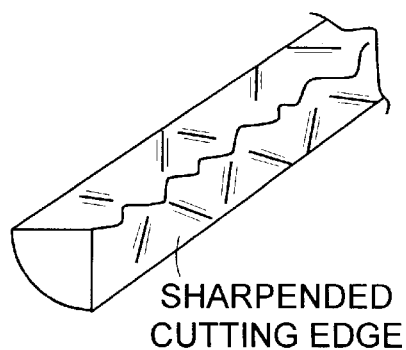
SHARPENDED
CUTTING EDGE
FIG. 7C

MEDICAL RETRIEVAL BASKET WITH LEGS SHAPED TO ENHANCE CAPTURE AND REDUCE TRAUMA

CROSS REFERENCE TO RELATED APPLICATIONS

This is based on, and claims priority to, provisional U.S. patent application ser. No. 60/060,830 which was filed on Oct. 1, 1997. This also is based on, and claims priority to, two other provisional U.S. patent applications filed on that date, namely, ser. No. 60/060,819 filed on Oct. 1, 1997 and ser. No. 60/060,821 filed on Oct. 1, 1997.

TECHNICAL FIELD

The invention relates generally to baskets for retrieving material in a body. More particularly, the invention relates to urology baskets having legs with a certain cross-section designed to retrieve kidney stones, urinary calculi, choleliths, or the like from within the body while causing less trauma to the body and enhancing stone capture.

BACKGROUND INFORMATION

Baskets are used to retrieve various foreign or biological materials (e.g., kidney stones, urinary calculi, choleliths, etc.) from within a body. Baskets are used in the field of urology and other areas such as, for example, endoscopy. Existing retrieval baskets typically include a plurality of wires (or legs) which truncate at a base of the basket. It is known to form the legs of the basket from wire having a rectangular cross-section (FIG. 5A) or a round cross-section (FIG. 5B). The legs are joined by solder, weld, or mechanical means at the base of the basket and at its distal tip. At the base, the legs also are attached to a shaft coil (or wire). This coil is moved back and forth within a sheath or catheter by an actuation device (e.g., a proximal handle with a back-and-forth thumb-activated slider). By moving the coil forward with the actuation device, the legs are extended out of the distal end of the catheter and thus allowed to expand and form the basket shape beyond the distal end of the catheter. Moving the coil back causes the basket to retract into the catheter.

SUMMARY OF THE INVENTION

In general, the advantages of basket legs having a rectangular cross-section include good dilatation force and good contact between the inner surface of the legs and the stone, and the disadvantages of such legs include sharp edges (i.e., the top two corners of the rectangle that contact the interior wall of the lumen in which the basket is disposed) and thus tissue trauma, inability to rotate the basket due to the danger of tissue trauma, and the difficulty of forming a helix-shaped basket structure when the basket is expanded. In general, the advantages and disadvantages of basket legs having a round (or circular) cross-section are the opposite of those encountered with legs of rectangular cross-section. That is, the advantages of legs of round or circular cross-section generally include round edges and thus reduced tissue trauma, ability to rotate the basket without danger of tissue trauma, and ability to form a helix-shaped basket structure, and the disadvantages of legs of round cross-section generally include less dilatation force and less contact between the inner surface of the legs and the stone being captured.

The invention relates to a medical retrieval basket having legs with a cross sectional shape designed to enhance the capture and retrieval of foreign materials or biological materials (e.g., kidney stones, urinary calculi, etc.) from within a body while causing less trauma to tissue. The two basic design objectives according to the invention are (1) to cause less trauma to body tissues and to the linings of lumens of the body in which the basket is placed and manipulated to accomplish the retrieval of material and (2) to enhance the material-capturing ability of the basket. One shape that meets the two basic design goals of the invention is a basket having legs with a D-shape in cross-section. Advantages of the D-shape, and all other shapes according to the invention, include less trauma to tissue, ability to rotate the basket without forming the legs in a helix configuration, improved stone purchase and contact, ability to use the basket for tissue biopsy because of its improved cutting ability, improved stone breaking and/or crushing ability, ability to reduce the overall size of the catheter basket device while maintaining or increasing the opening force of the basket, and improved dilatation force compared to a basket with legs of round cross-section while making the basket less tissue traumatic.

In accordance with the invention, a medical retrieval device, and related method, uses a basket formed by one or more legs to retrieve foreign or biological material. At least one of the legs has at least two surfaces, namely, an inner surface and an outer surface. The outer surface is an atraumatic surface such as a curved surface. The atraumatic outer surface can include one or more radii. The inner surface can be flat such that the leg has a D-shaped cross section. Other shapes are possible for the inner surface including a pointed shape that enhances the basket's stone crushing or breaking ability. The inner surface, whatever its shape, can have a smooth surface, or it can have a rough surface (e.g., serrated, etched, toothed, etc.) for further enhancing the basket's ability to capture material such as stones and other calculi.

In one aspect, the invention involves a medical retrieval device. The device comprises a basket that includes one or more legs that form the basket. At least one of the legs comprises at least two surfaces wherein at least one of the two surfaces comprises a curved surface.

Embodiments of this aspect of the invention can include the following features. For example, the leg with the at least two surfaces can have a cross section defined by the surfaces, and the cross section can comprise a D-shape defined by the surfaces wherein the curved surface comprises an outer surface and the other surface comprises an inner surface. In general, the curved surface can comprise an outer surface and the other surface can comprise an inner surface. The inner surface can comprise a flat surface such that the cross section comprises a D-shape, or the inner surface can be wedge-shaped and comprise at least one point. Also, the inner surface can comprise a surface that is rougher than the outer surface, and this rough inner surface can comprise, for example, a serrated surface, a toothed surface, or an etched surface. The curved surface can comprise more than one radius (e.g., a B-shape). The basket can have three or more legs.

In another aspect, the invention relates to a medical retrieval device that comprises a basket having one or more legs forming the basket. At least one of the legs comprises at least an inner surface and an outer surface wherein the outer surface comprises an atraumatic surface.

Embodiments of this aspect of the invention can include a curved surface as the outer atraumatic surface. Other embodiments of this aspect of the invention can include other features such as those described above for the previous aspect of the invention.

In still another aspect, the invention involves a method for retrieving material from a body. The method comprises inserting an extractor into a body. The extractor comprises a basket having one or more legs forming the basket, and at least one of the legs comprises at least an inner surface and an outer surface wherein the outer surface comprises an atraumatic surface. The method further comprises capturing the material with the basket. The captured material contacts the inner surface of at least one of the legs. The method further comprises withdrawing the extractor from the body to remove the captured material from the body.

Embodiments of this aspect of the invention can include the following features. For example, the capturing step can comprise capturing a calculus such as, for example, a kidney stone, a ureteral stone, a urethral stone, a urinary bladder stone, or a stone in the biliary tree such as a gallbladder stone or a bile duct stone. Also, the capturing step can further comprise breaking the material into two or more pieces with, for example, a sharpened inner surface.

In yet another aspect, the invention relates to a medical retrieval device that comprises a basket having one or more legs that form the basket. At least one of the legs comprises at least an inner surface, and at least a portion of the inner surface is adapted to contact material (e.g., calculi) and is rough. The rough inner surface can be, for example, a serrated surface, a toothed surface, or an etched surface.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 5A and 5B are examples of legs of prior art baskets which include flat or rectangular cross-section legs (FIG. 5A) and round or circular cross-section legs (FIG. 5B).

FIG. 6A shows one embodiment of basket legs according to the invention, namely, D-shaped legs, the view being a cross section along "cross sections" in FIG. 4.

FIG. 6B shows an inner surface of one of the basket legs of FIG. 6A, where the inner surface is rough to further enhance capture.

FIGS. 7A and 7B together show another embodiment of basket legs according to the invention, namely, V-shaped legs with atraumatic rounded outer surfaces, the views being cross sections along "cross sections" in FIG. 4.

FIG. 7C shows an inner surface of one of the basket legs of FIGS. 7A and 7B.

DESCRIPTION

Figure 1:
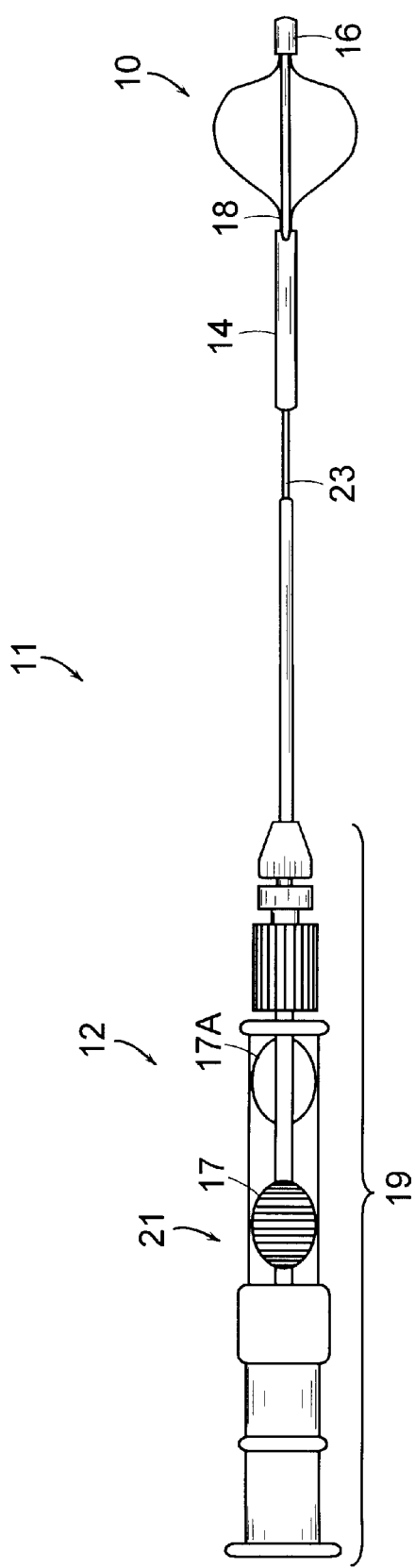
FIG. 1 is a plan view of a surgical extractor with a handle at a proximal end and a retrieval basket at a distal end.

Referring to FIG. 1, a basket 10 for retrieving biological material or foreign material is attached to an actuation device 12 via a sheath or catheter 14. The basket 10 includes a plurality of legs (or wires) attached at a basket tip 16 and base 18. At the base 18, the legs are also attached to a shaft coil, cable, or wire 23 located in the sheath 14. This cable 23 is actuated by the actuation device 12 (e.g., a slider 21 on a proximal handle 19) to move the cable 23 and thus the basket legs, and the basket 10 thus is advanced and retracted by use of the actuation device 12.

More particularly, with continued reference to FIG. 1, the basket 10 typically is part of a distal end of an extractor 11 which an operator (e.g., a physician) introduces into a patient in a form in which the basket 10 is retracted. In the retracted state, the sheath 14 retains the basket 10 in a compact form until the extractor 11 is positioned proximate to material to be retrieved such as, for example, a kidney stone, a ureteral stone, urethral stone, a bladder stone, a gallbladder stone, cholelith or bile duct stone. The operator holding the handle 19 moves the slider 21 connected to the sheath 14 from the position 17A shown in phantom to the position 17. In the position 17A, the basket 10 is fully deployed out of the sheath 14, and it is fully retracted when the slider 21 is in the position 17. The basket 10 is shown fully deployed in FIG. 1. With the basket 10 fully deployed and extending out of the end of the sheath 14, the surrounding tissue is dilated and the basket 10 assumes a structure that can be manipulated over the material (e.g., a calculus). The operator then manipulates the retrieval basket 10 via the proximally extending control cable 23 connected to the wires or legs of the basket 10 and captures material in the basket 10. After capture, the sheath 14 advances distally and reduces the volume of the retrieval basket 10 until it contacts the entrapped material so the operator can withdraw the extractor 11 with the entrapped material.

Known cross-sectional shapes for basket legs are rectangular (FIG. 5A) or round (FIG. 5B). However, in accordance with the invention and as shown in FIGS. 6 and 7, the basket 10 can have D-shaped legs (i.e., legs that each have a rounded outer surface and a flat inner surface) or V-shaped legs (i.e., legs that each have a rounded outer surface and an inner surface with a wedge shape and a point). Other leg shapes according to the invention are shown in FIG. 8. Whatever the particular leg shape, the shape will, according to the invention, (1) introduce less trauma and (2) enhance material capture. Also, whatever the particular leg shape, the legs can be drawn or ground or formed in a variety of other ways to achieve the shape. The legs can extend along a generally linear or helical path as described, for example, in U.S. Pat. No. 5,658,296. The entirety of this issued U.S. patent is hereby incorporated herein by reference.

Figure 2:
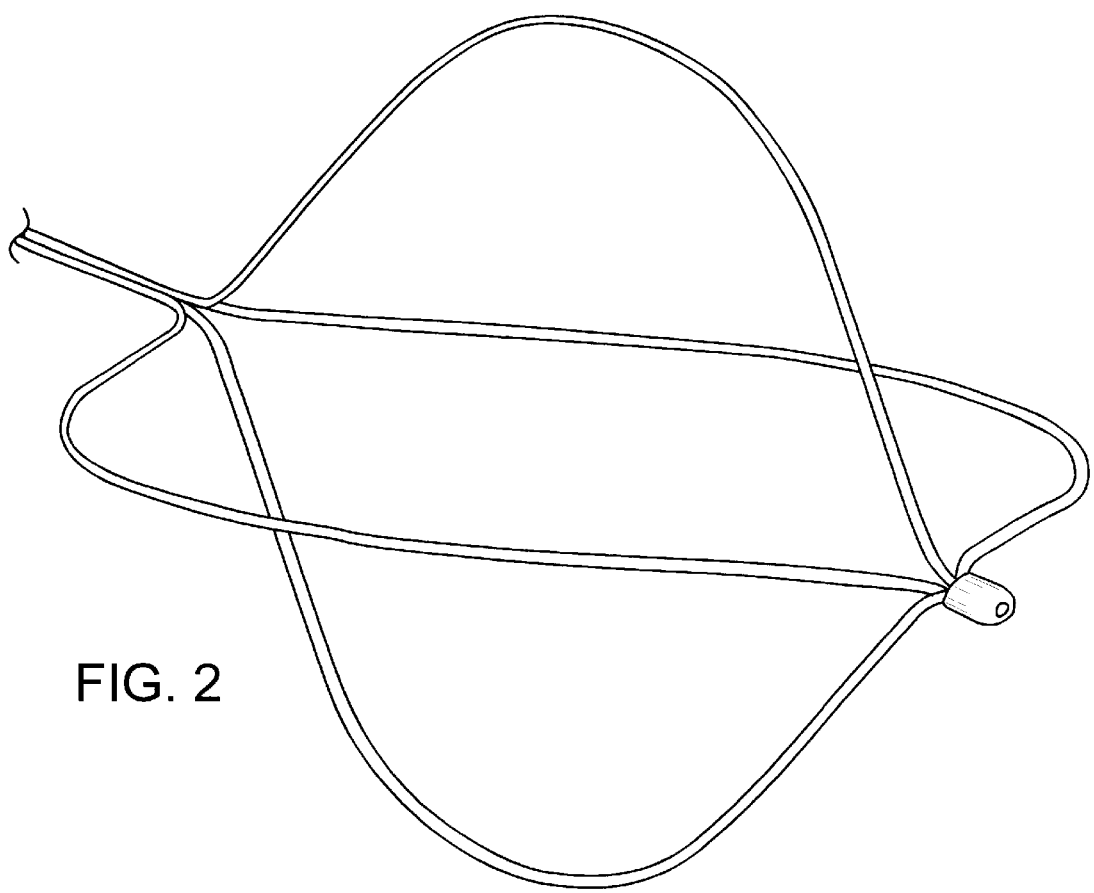
FIG. 2 is a perspective view of an expanded basket with D-shaped legs according to the invention.
Figure 3:
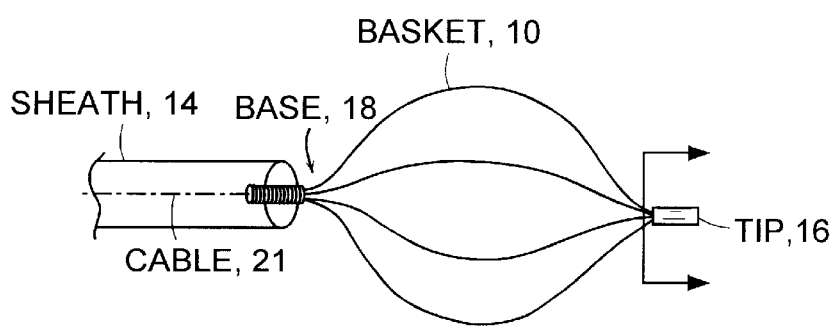
FIG. 3 is a plan view of the distal/basket end of the extractor of FIG. 1.
Figure 4:
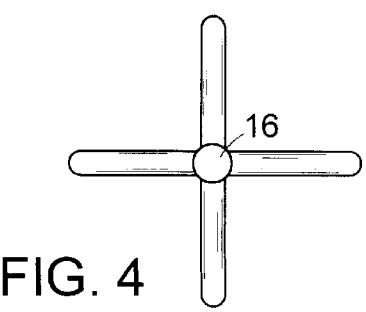
FIG. 4 is an end view of the extractor showing the tip of the basket and the four legs extending therefrom.

Referring to FIG. 2, the basket 10 of FIG. 1 is shown expanded. This particular basket has four D-shaped legs. In general, the basket 10 is formed by one or more legs, and it typically is formed by at least three legs. A simplified view of this basket is also shown in FIGS. 3 and 4. In those drawings, FIG. 3 shows just the distal end of the extractor 11, and FIG. 4 shows the legs of the basket 10 when viewed from the tip 16 down the length of the extractor 11.

Referring to FIGS. 6A and 6B, which like FIGS. 7A–7C and 8A–8E are cross sections taken generally along the cut labeled "cross sections" in FIG. 3, one disclosed embodiment of a basket according to the invention includes four D-shaped legs (FIG. 6A). The inner surface of one or more of these D-shaped legs can be rough so as to enhance the stone-capturing and holding ability of the basket. The roughness can be created in a variety of manners including serrations, teeth, etching, etc. on the inner surface(s). In FIG. 6B, teeth are shown on the inner surface of one of the D-shaped legs of FIG. 6A. Even without the rough inner surface, the D-shape, with its flat inner surface, enhances the ability of the basket to engage and hold stones. The outer surface of each of the D-shaped legs is rounded to form a smooth, atraumatic outer surface. The leg shape of FIG. 6A thus meets the two basic goals of any design in accordance with the invention, and that is less trauma and enhanced capture. The shape of the legs shown in FIG. 6A is a kind of hybrid between the known rectangular shaped legs (FIG. 5A) and the known round shaped legs (FIG. 5B), and the D-shaped legs of FIG. 6A generally have the advantages of each of these types of known legs without the disadvantages associated with the rectangular and round leg shapes. That is, the advantages of a basket with the D-shaped legs of the invention include increased dilatation force, better contact between the inner surface of the legs and the stone, atraumatic edges and thus reduced tissue trauma, ability to rotate the basket without danger of tissue trauma thereby increasing the ability to access and capture calculi disposed in difficult-to-reach locations, and ability to form easily a helix-shaped basket structure or a non-helix-shaped basket structure, and such a basket according to the invention lacks the disadvantages of sharp traumatic outer surface edges, inability to rotate the basket due to the danger of tissue trauma, difficulty in forming a helix-shaped basket structure, weak dilatation force, and poor contact between the inner surface of the legs and the stone being captured.

Although the outer surfaces of the basket legs are shown in FIG. 6A as being rounded it is possible to utilize other shapes for the outer surface and still be within the scope of the invention. For example, in FIG. 6A, the rounded outer surface could be replaced with any curved surface (e.g., a B-shape). In general, any type of outer surface is possible as long as it furthers one of the two goals of the invention which is to reduce trauma to the body to something less than that provided by the generally traumatic two-corner shape of the outer surface of the conventional rectangular wire basket legs. In general, a curved outer surface will satisfy this design requirement of the invention.

Figure 8B:
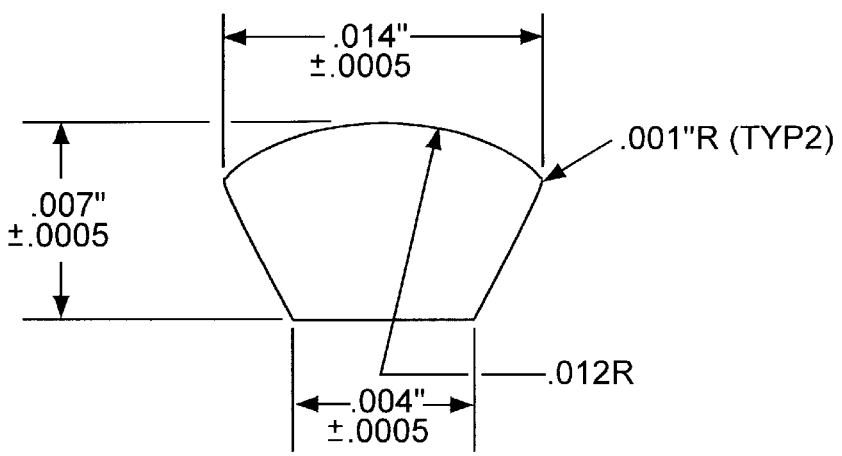
FIGS. 8A–8E are various other possible cross-sectional shapes for the basket legs in accordance with the invention, the views being cross sections along "cross sections" in FIG. 4.
Figure 8A:
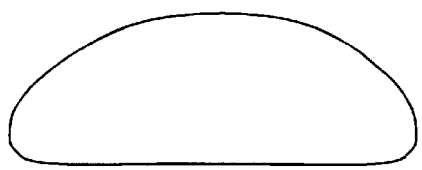
Figure 8C:
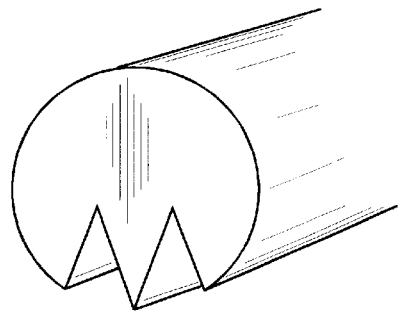
Figure 8E:

Also, although the inner surfaces of the basket legs are shown in FIG. 6A as being flat, it is possible to utilize other shapes for the inner surface and still be within the scope of the invention. For example, in FIG. 6A, the flat inner surface could be replaced with a concave surface such that the D-shape becomes a crescent shape (FIG. 8E). In general, any type of inner surface is possible as long as it furthers the second of the two goals of the invention which is to enhance the capturing and holding ability of the basket over that of the generally poor performance of conventional round wire basket legs. Also, any type of inner surface according to the invention can be smooth or it can be rough as described above.

Some additional basket leg shapes according to the invention are shown in FIGS. 7A–7C and 8A–8E and are described below with reference to those drawings. In general, these, and the other specific shapes disclosed herein, are just some of the possible leg shapes according to the invention.

Referring to FIGS. 7A and 7B, another disclosed embodiment of a basket according to the invention includes four generally V-shaped or wedge-shaped legs. As with the D-shaped wires of FIGS. 6A and 6B, the inner surface of one or more of these legs can be rough so as to enhance the stone-capturing and holding ability of the basket, and the roughness can be created in a variety of manners including serrations, teeth, etching, etc. on the inner surface(s). In FIG. 7C, grooves are shown on the inner surface of one of the V-shaped legs of FIGS. 7A and 7B. Even without the rough inner surface, the V-shape, with its point enhances the ability of the basket to engage and hold stones and to break and/or crush the stones if desired. In fact, the point or ridge on the inner surface of these wedge-shaped legs can be sharpened to form a cutting edge that will easily and firmly grip into calculi when the basket is collapsed therearound and that can cut or bite into stones to break and/or crush them into two or more pieces. As with the D-shaped wire of FIGS. 6A and 6B, the outer surface of each of the V- or wedge-shaped legs is rounded to form a smooth, atraumatic outer surface. The leg shape of FIGS. 7A and 7B thus meets the two basic goals of any design in accordance with the invention, and that is less trauma and enhanced capture. Like the D-shaped legs of FIGS. 6A and 6B, the legs of FIGS. 7A–7C includes advantages such as increased dilatation force, better contact between the inner surface of the legs and the stone, atraumatic edges and thus reduced tissue trauma, ability to rotate the basket without danger of tissue trauma thereby increasing the ability to access and capture calculi disposed in difficult-to-reach locations, and ability to form easily a helix-shaped basket structure or a non-helix-shaped basket structure, and the legs of FIGS. 7A–7C have none of the disadvantages of known basket leg shapes such as sharp traumatic outer surface edges, inability to rotate the basket due to the danger of tissue trauma, difficulty in forming a helix-shaped basket structure, weak dilatation force, and poor contact between the inner surface of the legs and the stone being captured.

As discussed above for the D-shaped legs of FIG. 6A, although the outer surfaces of the basket legs shown in FIGS. 7A–7C are rounded, it is possible to utilize other shapes for the outer surface and still be within the scope of the invention. The same is true for any of the other shapes according to the invention including those shown in FIGS. 8A–8E and discussed below with reference to those drawings. For example, in FIGS. 7A and 7B, the rounded outer surface could be replaced with any curved surface (e.g., a B-shape). Again, in general, any type of outer surface is possible as long as it furthers one of the two goals of the invention which is to reduce trauma to the body to something less than that provided by the generally traumatic two-corner shape of the outer surface of the conventional rectangular wire basket legs, and a curved outer surface satisfies this design requirement of the invention.

Also and as discussed above for the D-shaped legs of FIG. 6A, although the inner surfaces of the basket legs are shown in FIGS. 7A–7C as being V- or wedge-shaped, it is possible to utilize other shapes for the inner surface and still be within the scope of the invention. The same is true for any of the other shapes according to the invention including those shown in FIGS. 8A–8E and discussed below with reference to those drawings. Again, in general, any type of inner surface is possible as long as it furthers the second of the two goals of the invention which is to enhance the capturing and holding ability of the basket over that of the generally poor performance of conventional round wire basket legs. Also, any type of inner surface according to the invention can be smooth or it can be rough as described above.

Figure 8D:
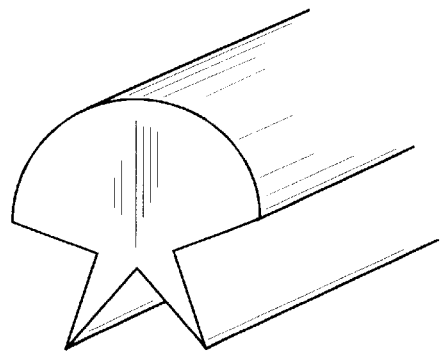

Referring to FIGS. 8A–8D, other possible cross-sectional shapes for the basket legs according to the invention include a modified D-shape (FIG. 8A), a shape that is part round and part trapezoidal (FIG. 8B), and a variety of other shapes including, for example, a two-groove shape (FIG. 8C) and a two-prong shape (FIG. 8D).

The cross-sectional shape of any of the basket legs can vary along the length of the leg. Also, a single basket can have individual legs of different shape such as, for example, one D-shaped leg, one B-shaped leg, and a third leg with the shape of FIG. 8B. Further, the various shapes according to the inventions can be formed by the basket legs themselves (as shown) or by other means such as coatings including, for example, teflon on the outer surface and/or rubber on the inner surface.

As indicated previously, the inner surface of each of the basket legs can be smooth or rough. Also, the inner surface can be rough along the entire length of the basket leg or for only a portion of the basket leg. These are true whatever the shape of the legs and whether or not they vary in shape along their length. In fact, even conventional basket legs can benefit from this enhancement, and thus rough inner surfaces of basket legs generally are a part of this invention. That is, roughening all or a portion of one or more of the inner surfaces of one or more of the legs of a conventional basket or of a basket as described herein forms a part of this invention. A retrieval basket having all or a portion of one or more of the inner surfaces of one or more of the basket legs roughened in accordance with the invention provides the benefits of increased stone capture and retention. All or a portion of the inner surface of any leg of any basket can be made rough in accordance with this invention by a variety of means including forming serrations on the inner surface of the leg, forming teeth on the inner surface of the leg, etching the inner surface of the leg to make it pitted and rough, sand blasting the inner surface of the leg, and a variety of other known techniques.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical retrieval device, comprising:
   a proximal handle;
   a sheath including a proximal portion, a distal end, and a lumen, the sheath extending distally from the handle; and
   a basket, the basket and the sheath moveable relative to each other to achieve a retracted position in which the basket is collapsed within the lumen of the sheath, and an extended position in which the basket extends from the distal end of the sheath, the basket comprising at least three wires, the wires joined at a distal end of the basket for capturing material when the basket is in the extended position, and for holding material when the basket is at least partially collapsed in the sheath, at least one of the wires comprising an inner surface and an outer surface, wherein at least a portion of said inner surface is flat and at least a portion of said outer surface is curved, and wherein the basket is positioned at the distal end of the device for capturing material in a body.

2. The device of claim 1 wherein the inner surface comprises a flat surface such that a cross-section of said wire comprises a B-shape.

3. The device of claim 1 wherein the outer surface comprises at least one curved surface.

4. The device of claim 1 wherein the inner surface comprises a flat surface such that a cross section of said wire comprises a D-shape.

5. The device of claim 1 wherein the inner surface comprises at least one tooth.

6. The device of claim 1 wherein the inner surface comprises a surface that is rougher than the outer surface.

7. The device of claim 1 wherein the inner surface is rough.

8. The device of claim 7 wherein the rough inner surface comprises a serrated surface.

9. The device of claim 7 wherein the inner surface comprises a plurality of teeth.

10. The device of claim 7 wherein the rough inner surface comprises an etched surface.

11. The device of claim 1 wherein the outer surface comprises more than one radius.

12. The medical retrieval device of claim 1 wherein the flat inner surface has at least a portion adapted to contact material, the portion of the inner surface being a rough surface.

13. The device of claim 2 wherein the inner surface comprises a serrated surface.

14. The device of claim 4 wherein the inner surface comprises a toothed surface.

15. The device of claim 4 wherein the inner surface comprises an etched surface.

16. The device of claim 3 wherein the curved surface comprises more than one radius.

17. The device of claim 4 wherein the radius of the outer surface is greater than or equal to 0.012 inches and less than or equal to 0.014 inches.

18. The device of claim 4 wherein the flat surface of the cross-section is 0.004±0.0005 inches in length.

19. The device of claim 4 wherein the radius of the curved surface is greater than or equal to 0.012 inches and less than or equal to 0.014 inches and the flat surface of the cross-section is 0.004 inches±0.0005 inches in length.

20. A method for retrieving material from a body, comprising:
    inserting an extractor into a body, the extractor comprising a proximal handle; a sheath including a proximal portion, a distal end, and a lumen, the sheath extending distally from the handle, and a basket, the basket and the sheath moveable relative to each other to achieve a retracted position in which the basket is collapsed within the lumen of the sheath, and an extended position in which the basket extends from the distal end of the sheath, the basket comprising at least three wires, the wires joined at a distal end of the basket for capturing material when the basket is in the extended position, and for holding material when the basket is at least partially collapsed in the sheath, at least one of the wires comprising an inner surface and an outer surface wherein at least a portion of said inner surface is flat and at least a portion of said outer surface is curved, and wherein the basket is positioned at the distal end of the device for capturing material in a body,
    capturing the material with the basket; and
    withdrawing the extractor from the body to remove the captured material from the body.

21. The method of claim 20 wherein the step of capturing the material comprises capturing a calculus.

22. The method of claim 21 wherein the step of capturing the calculus comprises capturing a kidney stone.

23. The method of claim 21 wherein the step of capturing the calculus comprises capturing a ureteral stone.

24. The method of claim 21 wherein the step of capturing the calculus comprises capturing a bladder stone.

25. The method of claim 21 wherein the step of capturing the calculus comprises capturing a stone in the biliary tree.

26. The method of claim 20 wherein the capturing step further comprises breaking the material into two or more pieces with the basket.

27. A medical retrieval device, comprising:

a proximal handle;

a sheath including a proximal portion, a distal end, and a lumen, the sheath extending distally from the handle; and a basket, the basket and the sheath moveable relative to each other to achieve a retracted position in which the basket is collapsed within the lumen of the sheath, and an extended position in which the basket extends from the distal end of the sheath, the basket comprising at least three wires, the wires joined at a distal end of the basket for capturing material when the basket is in the extended position, and for holding material when the basket is at least partially collapsed in the sheath, at least one of the wires comprising an inner surface and an outer surface, wherein said inner surface and said outer surface are curved and a cross-section of said wire comprises a crescent shape.

* * * * *